United States Patent
Duflot et al.

(10) Patent No.: US 8,101,806 B2
(45) Date of Patent: Jan. 24, 2012

(54) GRANULATED SORBITOL AND PROCESS FOR ITS PREPARATION

(75) Inventors: Pierrick Duflot, La Couture (FR); Baptiste Boit, Bethune (FR); Philippe Lefevre, Haverskerque (FR); José Lis, La Gorgue (FR)

(73) Assignee: Roquette Freres, Lestrem (FR)

( * ) Notice: Subject to any disclaimer, the term of this patent is extended or adjusted under 35 U.S.C. 154(b) by 465 days.

(21) Appl. No.: 12/375,464

(22) PCT Filed: Jul. 23, 2007

(86) PCT No.: PCT/FR2007/051707
§ 371 (c)(1),
(2), (4) Date: Jan. 28, 2009

(87) PCT Pub. No.: WO2008/012465
PCT Pub. Date: Jan. 31, 2008

(65) Prior Publication Data
US 2009/0324794 A1    Dec. 31, 2009

(30) Foreign Application Priority Data
Jul. 28, 2006  (FR) ..................... 06 06954

(51) Int. Cl.
*C07C 31/18* (2006.01)
*A23L 1/236* (2006.01)

(52) U.S. Cl. ......... 568/851; 568/852; 568/853; 426/548

(58) Field of Classification Search .................. 568/851, 568/852, 853; 426/548
See application file for complete search history.

(56) References Cited

U.S. PATENT DOCUMENTS

| 3,973,041 | A | * | 8/1976 | DuRoss | ............................. 426/3 |
| 4,252,794 | A | * | 2/1981 | DuRoss | ......................... 514/777 |
| 6,274,778 | B1 | | 8/2001 | Moraly et al. | |

FOREIGN PATENT DOCUMENTS

| EP | 1 008 602 | 6/2000 |
| GB | 2 046 743 | 11/1980 |

OTHER PUBLICATIONS

International Search Report dated Jan. 16, 2008, from corresponding PCT application.

* cited by examiner

*Primary Examiner* — Sikarl Witherspoon
(74) *Attorney, Agent, or Firm* — Young & Thompson

(57) ABSTRACT

The present invention relates to a granulated sorbitol of essentially γ crystalline form and having a high sorbitol content, characterized in that it has a specific surface area, determined according to the BET method, of greater than or equal to 2 $m^2/g$, preferably of between 2.2 and 4 $m^2/g$, and even more preferably of between 2.5 and 3.5 $m^2/g$, a compressibility of between 200 and 400 N, preferably of between 250 and 350 N, and a volume-average diameter, measured by laser diffraction particle sizing using a dry-system module, of between 260 and 1000 μm, preferably of between 260 and 500 μm, and even more preferably of between 260 and 350 μm.

9 Claims, No Drawings

GRANULATED SORBITOL AND PROCESS FOR ITS PREPARATION

FIELD OF THE INVENTION

A subject of the present invention is a granulated sorbitol in essentially γ (gamma) crystalline form with a high sorbitol content, having a particular specific surface, compressibility and particle size.

Within the meaning of the invention, by "essentially γ crystalline form" is meant a content sorbitol crystal in γ form of greater than 95% by weight, preferably greater than 98% by weight, even more preferentially greater than 99% by weight.

Determining the nature of the crystalline forms of granulated sorbitol according to the invention can be carried out by microcalorimetric analysis or DSC (Differential Scanning Calorimetry), a technique which principally makes it possible to determine the heat of fusion (enthalpy of fusion or ΔHf) and melting temperature (Tf) of polymorphs of the products subjected to analysis. The 5 crystalline forms of sorbitol, i.e. the α, β, γ, δ and ε forms, are characterized by their respective melting temperature. The analysis is carried out on 6 mg of sample product for analysis, finely ground using a laboratory mortar, placed in an aluminium crucible having a capacity of 40 μl, crimped and pierced with a hole (Mettler type DSC 821e measurement device). The temperature increase program consists of passing from 10° C. to 110° C. at the rate of 2° C. per minute. The crystalline forms of granulated sorbitol according to the invention are identified on the DSC thermogram in the melting temperature range comprised between 98 and 99.5° C. for the γ crystalline form. For integration of the melting peaks corresponding to the γ form, the following procedure is carried out: integration of the melting peak by using the base line to the right of the peak. The determination is carried out by using a standard measurement software program, by calculating the heat (enthalpy) of fusion (ΔHf in J/g) and the melting temperature (Tf) at the top of said peak.

The percentage by weight of the γ crystalline form fraction of the granulated sorbitol is determined by the ratio of the enthalpies of fusion of each of the crystalline forms to the sum of the measured enthalpies of fusion for a given sample.

Within the meaning of the invention, by a "high sorbitol content" is meant a sorbitol content greater than 98%, preferably greater than 98.5% by weight, even more preferentially comprised between 98.5 and 99.5% by dry weight.

The present invention also relates to a granulated sorbitol having a very particular hygroscopicity, density and flow properties.

Finally, the invention relates to a granulated sorbitol having improved technical properties for use as an flavouring medium and under direct compression, as well as a process for its preparation.

BACKGROUND OF THE INVENTION

Sorbitol is a hexitol principally used in the fields of food industry and pharmaceutical applications as an artificial sweetener, but also for its reduced calorie content and acariogenicity.

Sorbitol, like other polyols such as xylitol or mannitol, is commonly used as a pharmaceutical excipient, as a sweetener and texturizer in the food industry, and as an additive medium in all types of industries. However it is a better excipient than xylitol and mannitol, in particular under compression, as a result of its particular ability to crystallize in the form of directly compressible needle crystals.

Generally, in order to have available a crystallized sorbitol with high compression resistance, it is necessary to produce a γ crystalline form of sorbitol (α- and β-forms are particularly unstable) by working with a supersaturated sorbitol solution, in which the γ form represents at least 90%.

However, even when it is crystallized in this more stable γ form, the granulated sorbitol obtained in a standard fashion has a certain number of drawbacks, including that of being very hygroscopic.

This high hygroscopicity results in the flow of the granulated sorbitol becoming difficult, even impossible, whenever water uptake has occurred.

In order to avoid this problem of the flow of granulated sorbitol, it was recommended in patent FR 1,506,334 to prepare a low-density sorbitol with a higher particle size (comprised between 0.42 and 1.19 mm).

However, it has been established that as the bulk density of a granulated sorbitol decreases, the more friable it becomes, i.e. affected by an alteration in its particle size by mechanical action. Moreover, the dissolution times of this granulated product with a coarse particle size are generally too long and therefore unsuitable.

Finally, although the flow properties are partially improved by using particles of such a particle size, the residual hygroscopic character which is still too high militates against the use of this granulated sorbitol in all cases where it is combined with ingredients or additives which are highly affected by water.

It is also established that the ability to fix large quantities of additives is a direct function of the specific surface area of said particles.

The absorption capacities of the granulated sorbitol are thus greater as its specific surface area increases. However, it is known that the specific surface area of the dense crystals of commercial γ sorbitol is very low.

Thus, for a particle size comprised between 500 and 1000 μm, it is equal to 0.7 $m^2$/g at most.

With the aim of preparing a dry sorbitol having a better particle size, good flow properties and satisfying the desired conditions of compressibility, patent application FR 2,622,190 describes a sorbitol powder containing particles having a relatively high average diameter comprised between 350 and 500 μm.

However, the high bulk density and the low specific surface area, of the order of 0.9 a 1.2 $m^2$/g, are not significantly modified by the spray manufacturing process used, such that the sorbitol thus obtained retains the same moisture adsorption factor and the same solubility in water as the starting sorbitol powder.

Patent EP 32,288 describes a polymorph of sorbitol having a disrupted and loosely-packed crystalline structure, presenting an improved hygroscopicity and satisfactory compression properties. However, these particular properties only relate to a particle size fraction comprised between 250 and 841 μm (i.e. 60/20 mesh), the specific surface area of which is in any case less than 2 $m^2$/g.

Patent EP 380,219 describes free-flowing polymorphic forms of sorbitol having a specific surface area which can reach 5 $m^2$/g, the apparent density of which is high (up to 0.7 g/ml) and the solubility rate in water satisfactory.

However, in order to achieve this result, it is necessary to prepare, by spraying open-centred spherules of acicular microcrystals of thickness less than 1 μm and length comprised between 5 and 20 μm.

Moreover, it is recommended in this patent to use sorbitol/mannitol mixtures or to add saccharose.

It can be seen from all of the above that there is an unmet need for a granulated sorbitol having a specific surface area and a compressibility as high as possible, while maintaining a satisfactory particle size, density and free flow.

Thus by devising and preparing a new granulated sorbitol at the cost of much research, the Applicant has creditably reconciled all these aims hitherto regarded as irreconcilable.

SUMMARY OF THE INVENTION

The granulated sorbitol according to the invention is thus firstly characterized in that it has:
- a specific surface area, determined according to the BET process, greater than or equal to 2 m$^2$/g, preferably comprised between 2.2 and 4 m$^2$/g and even more preferentially comprised between 2.5 and 3.5 m$^2$/g,
- a compressibility comprised between 200 and 400 N, preferably comprised between 250 and 350 N,
- a volume average diameter measured by laser diffraction granulometry using a dry-route module comprised between 260 and 1000 µm, preferably between 260 and 500 µm and even more preferentially between 260 and 350 µm;

DETAILED DESCRIPTION OF THE INVENTION

The specific surface area over the 250-841 µm granulometric fraction of the granulated sorbitol is determined by using a Beckman-Coulter type SA3100 specific surface area analyser based on a nitrogen absorption test on the surface of the product subjected to analysis, according to the technique described in the article "BET Surface Area by Nitrogen Absorption" by S. Brunauer et al. (Journal of American Chemical Society, 60, 309, 1938).

The BET analysis is carried out at 3 points.

The granulated sorbitol according to the invention then has a specific surface area greater than or equal to 2 m$^2$/g, preferably comprised between 2.2 and 4 m$^2$/g and even more preferentially comprised between 2.5 and 3.5 m$^2$/g, which is remarkably high.

The compressibility of the granulated sorbitol is determined as follows.

Sorbitol tablets are prepared using a Frogerais AM alternating laboratory press equipped with round concave punches having a 13 mm diameter and 13 mm radius of curvature. The lubricant used is magnesium stearate at a rate of 1%.

The manufactured tablets have a constant thickness (5 mm) and variable weight, hence the variable tablet densities which make it possible to draw the hardness graphs as a function of the tablet density. The hardness is measured on an Erweka TBH30GMD hardness tester, and is expressed in Newtons. The compressibility of the granulated sorbitol according to the invention, measured for tablets of density 1.3 g/ml, is determined at a value comprised between 200 and 400 N, preferably comprised between 250 and 350 N.

As a result of this remarkable compressibility value, the mechanical strength of the tablets obtained with said granulated sorbitol according to the invention is very high, compared with that of the tablets obtained with the commercial products.

By way of example from the commercially available sorbitols, the Applicant has found that those having the highest specific surface area are in particular those marketed by Merck under the name Karion®, such as Karion® P 300 which has a specific surface area according to BET that can reach 3.4 m$^2$/g.

The compressibility of this sample, determined under the same conditions as those used to characterize the granulated sorbitol according to the invention, does not exceed a value of the order of 320 N.

As regards the sorbitol in powder form manufactured by the Applicant according to the teaching of its patent EP 1,008,602, although it has a compressibility, measured for tablets of density 1.3 g/ml, of the order of 275 N, this is for a sorbitol in powder form having an average particle diameter less than 200 µm and a specific surface area of 2.4 m$^2$/g.

The granulated sorbitol according to the invention is also characterized by its average volume diameter (arithmetical average) D4, 3, comprised between 260 and 1000 µm, preferably comprised between 260 and 500 µm, and even more preferentially comprised between 260 and 350 µm.

These values are determined on a Beckman-Coulter type LS 230 laser diffraction granulometer, equipped with its powder dispersion module (dry route), following the technical manual and the manufacturer's instructions.

The measurement range of the type LS 230 laser diffraction granulometer is from 0.04 µm to 2,000 µm.

The operating conditions of screw speed under the hopper and the intensity of vibration of the dispersion chute are determined such that the optical concentration is comprised between 4% and 12%, ideally 8%.

The results are calculated in % by volume, and expressed in µm.

To the knowledge of the Applicant, there is no granulated sorbitol in this granulometric fraction from 260 to 500 µm, which has such specific surface area and compression values.

Further, by way of example, the Merck Karion P300 sorbitol sample analysed by the Applicant has an average diameter comprised between 200 and 250 µm, and the sorbitol in powder form manufactured by the Applicant according to the teaching of its patent EP 1,008,602, itself has an average diameter comprised between 150 and 250 µm.

The granulated sorbitol of the invention has a hygroscopicity, determined by its change in weight between 60 and 0% relative humidity (RH), comprised between 1 and 2%.

The hygroscopicity measurement test in this case consists of assessing the weight variation of the sorbitol sample when it is subjected to different RH conditions at 20° C. in equipment manufactured by Surface Measurement Systems (London UK) and called Dynamic Vapour Sorption Series 1.

This equipment consists of a differential microbalance which makes it possible to quantify the change in weight of a sample in relation to a reference (here the reference pan of the differential balance is empty) when the latter is subjected to different climatic conditions.

The carrier gas is nitrogen, and the weight of the sample is comprised between 10 and 12 mg. The RH programs are 0% RH for 24 h (dehydration) then 10, 20, 30, 35, 40, 45, 50, 52, 54, 56, 58 and 60% RH. The stability factor which makes it possible to pass automatically from one RH to the next is the dm/dt ratio which is set to 0.002%/mn for 20 minutes.

Finally, a table of values is obtained, corresponding for each RH to the equation $[(m-m_0)/m_0] \times 100$ where "m" is the mass of the sample at the end of the test for the RH considered and "$m_0$" the mass at the end of dehydration.

The results are expressed as the difference between the values for the change in weight (as described above) obtained respectively at 60% and after dehydration (at 0% RH).

It is particularly surprising that a granulated sorbitol can have both a specific surface area greater than or equal to 2 m$^2$/g, preferably comprised between 2.2 and 4 m$^2$/g, even more preferentially comprised between 2.5 and 3.5 m$^2$/g, and such a low hygroscopicity, i.e. comprised between 1 and 2%.

In fact, it is conventionally accepted that the hygroscopicity of a product increases with its specific surface area, i.e. its surface exposed to the medium containing water vapour.

Nevertheless, granulated sorbitol according to the invention has a high specific surface area, characteristic of a granulated product, with a low hygroscopicity, characteristic of a product crystallized in a stable crystalline form.

By way of example, the sample of Karion P 300 sorbitol marketed by Merck and analysed by the Applicant has a hygroscopicity of 2.4% for a specific surface area according to BET of 3.4 m$^2$/g.

The granulated sorbitol according to the invention is also characterized by its density and its free flow.

The density of the granulated sorbitol according to the invention is calculated by determining the ratio between the mass of the sample to be analysed and the volume that it occupies after a free flow in a container and at a given temperature.

More precisely, a volume of a sample contained in a 250 ml test tube is measured at ambient temperature and said volume determined by measuring the mass of an equal volume of water at ambient temperature.

After washing and drying the test tube, it is weighed with an accuracy of 0.1 g (determining the original mass or $m_0$), filled to the top with water and weighed again (i.e. mass $m_1$).

Said test tube is emptied, washed and dried again, and the sample introduced into the test tube using a stainless steel pouring funnel (top diameter: 12 cm; internal diameter: 12 mm; cone height: 9 cm; tube length: 2 cm) arranged on a stand such that the height comprised between the funnel spout and the test tube is 10 cm.

The sample is then allowed to flow freely through the funnel into the test tube, until the latter is filled to the top.

The surplus product is leveled off using a spatula, so that a flat surface is obtained at the top of the test tube.

The test tube is removed and weighed with its contents, still with an accuracy of 0.1 g (i.e. mass $m_2$).

The density expressed in g/l is given by the following formula:

$$[(m_2-m_0)/(m_1-m_0)]\times\rho\times1000$$

where $\rho$ is the density in g/ml of the water at ambient temperature.

Under these conditions, the granulated sorbitol according to the invention has a density comprised between 350 and 650 g/l, preferably comprised between 400 and 550 g/l.

As regards the free flow of the granulated sorbitol according to the invention, it is determined according to the measurement process recommended by the European Pharmacopoeia (EP 5.0 vol 1, 01/2005: 20916 article 2.9.16).

The granulated sorbitol of the invention then has a free flow comprised between 5 and 20 seconds, preferably between 5 and 15 seconds.

This value is fully satisfactory, in comparison with those of the sorbitol powders of the prior art.

These technological properties as a whole make the granulated sorbitol according to the invention particularly suitable for use as a sweetener, texturizer, excipient and especially as an additive medium in compositions in the form of lozenges or tablets intended in particular for the food, pharmaceutical and industrial fields.

According to a first embodiment, the granulated sorbitol according to the invention is capable of being obtained by a step of spraying a sorbitol melt onto a sorbitol powder in a fluidized air bed granulator.

According to a second embodiment, the granulated sorbitol according to the invention is capable of being obtained by a step of spraying a sorbitol solution having a high dry matter content onto a sorbitol powder in a fluidized air bed granulator.

In order to obtain a granulated sorbitol according to the invention which has the functional characteristics described, the Applicant found it advisable to choose as a starting sorbitol, a sorbitol powder which can be obtained by crystallization from water or from another solvent such as alcohol, by sugar-coating, by atomization or by extrusion.

In the first embodiment, the melt is constituted by sorbitol having a dry matter greater than 98.5%, preferably greater than 99%, obtained by evaporation under vacuum of a sorbitol solution.

In the second embodiment, the sorbitol solution having a high dry matter content itself has a dry matter content comprised between 65 and 98.5%, preferably comprised between 70% and 98.5%, even more preferentially comprised between 90 and 98.5%.

Surprisingly and unexpectedly, the Applicant observed that the granulation of a sorbitol using a melt, or using a sorbitol solution having a high dry matter content, in a fluidized air bed granulator makes it possible, to prepare with a high yield a product according to the invention as regards its specific surface area and its compressibility, particle size and hygroscopicity, density and flow rate.

In fact, the processes described previously do not allow all of the desired characteristics to be obtained.

In order to carry out the granulation, a continuous fluidized air bed granulator can be used, for example.

Advantageously, a circular continuous fluidized air bed granulator with discharge pipe can be used, or a rectangular continuous one with piston flow, into which the sorbitol powder is continuously introduced, via a constant weight feeder, and the sorbitol melt or high dry matter content sorbitol to be sprayed are continuously introduced using a volumetric metering device.

As exemplified below, the Applicant chose to use a GLATT AGT-type continuous fluidized air bed granulator with classifying discharge pipe.

Good contact between the constituents and granulation of the melt or the sorbitol solution with a high dry matter content on the sorbitol powder particles is achieved by placing in suspension in an air stream.

Thus the sorbitol powder and the sorbitol melt, or the sorbitol solution with a high dry matter content, are granulated by coming into contact in the fluidized air bed equipped with a system for spraying liquids by injection nozzles, for example two-fluid.

At the outlet from the fluidized air bed granulator, the granules are continuously discharged. The discharge is carried out preferentially by the classifying discharge pipe of the AGT granulator, and by overflow, if the rectangular continuous granulator with piston flow is used.

The granulated sorbitol according to the invention is obtained after cooling and optionally sieving. In this case, the fines particles, also called the fines, can be directly recycled to the start of granulation and the large particles crushed in order to give the so-called crushed rejects then recycled to the start of sieving or the start of granulation.

A fraction of the granulated sorbitol according to the invention can also be crushed and recycled to the start of granulation.

In a preferred embodiment of the process according to the invention, the following successive steps are carried out:

a) optionally concentrating by evaporation a solution having a sorbitol dry matter content greater than 65%, preferably comprised between 65 and 75%, more preferentially 70%, in order to obtain a solution having a high dry matter content or a melt, b) introducing into a fluidized air bed granulator having a discharge pipe, said sorbitol melt or said sorbitol solution with a high dry matter content with a crystallized sorbitol in a ratio by weight of crystallized sorbitol:sorbitol melt or sorbitol solution with a high dry matter content greater than 0.5:1, preferably comprised between 1:1 and 2:1, c) granulating the crystallized sorbitol with said melt, at a fluidized air bed temperature greater than 65° C., preferably comprised between 75° C. and 85° C., d) recovering the granulated product thus obtained via the discharge pipe, e) cooling said granulated product thus obtained at ambient temperature, typically 20° C., for a duration comprised between 30 minutes and 2 hours, preferably equal to 1 hour, f) sieving and recovering the granulated sorbitol thus obtained.

Advantageously, the process can comprise the following subsequent step:

g) recycling the fines, the crushed rejects and a fraction of the granulated sorbitol thus obtained in order to maintain a ratio by weight of sorbitol powder:sorbitol melt or sorbitol solution with a high dry matter content greater than 0.5:1, preferably comprised between 1:1 and 2:1.

The invention also relates to the use of granulated sorbitol according to the invention as a sweetener, texturizer, excipient or especially as an additive medium in compositions in tablet form intended in particular for the food, pharmaceutical or industrial fields.

The invention also relates to a tablet manufactured from granulated sorbitol according to the invention. The sorbitol content of the tablet will depend on the desired usage of the tablet. Typically, the sorbitol content of the tablet can be comprised between 1% and 90%.

Other features and advantages of the invention will become apparent on reading the following examples. They are however given here purely by way of illustration, and are not limitative.

Example 1

A solution having a 70% sorbitol content on a dry-matter basis is placed under vacuum in an evaporation container in order to obtain a sorbitol melt having a dry matter content of 99%.

At the end of evaporation, the melt is maintained at a temperature of 120° C.

Then an AGT 400-type fluidized air bed granulator previously loaded with 25 kg of crystallized sorbitol is continuously fed via a powder flow metering device marketed by K-tron, at a flow rate of approximately 10 kg/h, with a crystallized sorbitol marketed by the Applicant under the trade name NEOSORB®, in order to obtain a volume average diameter of particles of 180 μm.

In addition, the continuous fluidized air bed granulator is fed with the sorbitol melt via a two-fluid spray nozzle at a flow rate of 10 kg/h.

Spraying of the melt is carried out by an air stream at 120° C. under a pressure of 5.5 bars.

The air used for placing the granulated sorbitol in suspension has a flow rate of approximately 850 m³/h and a temperature adjusted so that the temperature in the fluidized air bed is 80° C.

The granulated sorbitol is continuously discharged via the classifying discharge pipe (the air flow rate in the tube is adjusted to 60 m³/h in order to obtain the correct final particle size) in a fluidized air bed in order to provide cooling from 80° C. to 20° C. over one hour.

The granulated and cooled product is then continuously sieved on a rotary sieve equipped with two metal sieves of 100 and 500 μm.

The fines, crushed rejects and a fraction of the product obtained between 100 and 500 μm, itself also crushed, (crushing carried out in order to obtain an average recycling particle size of the order of 180 μm) are recycled to the start of granulation in order to maintain a total recycling flow of 10 kg/h.

The granulated sorbitol thus obtained has the characteristics shown in Table I below.

TABLE I

| Parameters | Granulated sorbitol of the invention |
| --- | --- |
| DSC analyses: | |
| γ form | |
| ΔHf (J/g) | 173 |
| Tf | 99.2 |
| Other forms | |
| ΔHf (J/g) | n/a |
| Specific surface area according to BET (m²/g) | 2.4 |
| Compressibility (N) (ERWEKA hardness of the tablets) | 270 |
| Average diameter LASER (μm) | 338 |
| Hygroscopicity | 1.10 |
| Density (g/l) | 483 |
| Free flow (s) | 12 |

Example 2

A solution having a 70% sorbitol content on a dry-matter basis is placed under vacuum in an evaporation container in order to obtain a sorbitol melt having a dry matter content of 99%.

At the end of evaporation, the melt is maintained at a temperature of 120° C.

Then an AGT 400-type fluidized air bed granulator previously loaded with 25 kg crystallized sorbitol is continuously fed via a powder metering device marketed by K-tron, at a flow rate of approximately 20 kg/h, with a crystallized sorbitol marketed by the Applicant under the trade name NEOSORB®, in order to obtain an average diameter of particles of 180 μm.

In addition, the continuous fluidized air bed granulator is fed with the sorbitol melt via a two-fluid spray nozzle at a flow rate of 10 kg/h.

Spraying of the melt is carried out by air at 120° C. under a pressure of 5.5 bars.

The air used for placing the granulated sorbitol in suspension has a flow rate of approximately 850 m³/h and a temperature adjusted so that the temperature in the fluidized air bed is 80° C.

The granulated sorbitol is continuously discharged via the classifying discharge pipe (the air flow rate is adjusted to 60 m³/h in order to obtain the correct final particle size) in a fluidized air bed in order to provide cooling from 80° C. to 20° C. over one hour.

The granulated and cooled product is then continuously sieved on a rotary sieve equipped with two metal sieves of 100 and 500 µm.

The fines, the crushed rejects and a fraction of the product obtained between 100 and 500 µm, itself also crushed, (crushing carried out in order to obtain an average recycling particle size of the order of 180 µm) are recycled to the start of granulation in order to maintain a total recycling flow of 20 kg/h.

The granulated sorbitol thus obtained has the characteristics shown in Table II below.

TABLE II

| Parameters | Granulated sorbitol of the invention |
| --- | --- |
| DSC analyses: | |
| γ form | |
| ΔHf (J/g) | 179 |
| Tf | 99.2 |
| Other forms | |
| ΔHf (J/g) | n/a |
| Specific surface area according to BET (m²/g) | 2.9 |
| Compressibility (N) (ERWEKA hardness of the tablets) | 275 |
| Average diameter LASER (µm) | 270 |
| Hygroscopicity | 1.11 |
| Density (g/l) | 523 |
| Free flow (s) | 7 |

Example 3

An AGT 400-type fluidized air bed granulator, previously loaded with 25 kg crystallized sorbitol, is continuously fed via a powder metering device marketed by K-tron at a flow rate of approximately 12 kg/h, with a crystallized sorbitol the Applicant under the trade name NEOSORB®, in order to obtain an average particle diameter of 180 µm.

In addition, the continuous fluidized air bed granulator is fed, via a two-fluid spray nozzle at a flow rate of 18 kg/h, with a sorbitol solution having 70% of dry matter at a temperature of 60° C.

Spraying of the solution is carried out by air at 90° C. under a pressure of 3 bars.

The air used for placing the granulated sorbitol in suspension has a flow rate of approximately 850 m³/h and a temperature adjusted so that the temperature in the fluidized air bed is 75° C.

The granulated sorbitol is continuously discharged via the classifying discharge pipe (the air flow rate in the pipe is adjusted to 60 m³/h in order to obtain the correct final particle size) in a fluidized air bed in order to provide cooling from 75° C. to 20° C. over one hour.

The granulated and cooled product is then continuously sieved on a rotary sieve equipped with two metal sieves of 100 and 500 µm.

The fines, the crushed rejects and a fraction of the product obtained between 100 and 500 µm, itself also crushed, (crushing carried out in order to obtain an average recycling particle size of the order of 180 µm) are recycled to the start of granulation in order to maintain a total recycling flow of 12 kg/h.

The granulated sorbitol thus obtained has the characteristics shown in Table III below.

TABLE III

| Parameters | Granulated sorbitol of the invention |
| --- | --- |
| DSC analyses: | |
| γ form | |
| ΔHf (J/g) | 165 |
| Tf | 98.7 |
| Other forms | |
| ΔHf (J/g) | 2 |
| Specific surface area according to BET (m²/g) | 2.6 |
| Compressibility (N) (ERWEKA hardness of the tablets) | 340 |
| Average diameter LASER (µm) | 328 |
| Hygroscopicity | 1.85 |
| Density (g/l) | 470 |
| Free flow (s) | 11 |

Example 4

A solution having a 70% sorbitol content on a dry-matter basis is placed under vacuum in an evaporation container in order to obtain a sorbitol solution having a dry matter content of 90%.

At the end of evaporation, the melt is maintained at a temperature of 110° C.

Then an AGT 400-type fluidized air bed granulator previously loaded with 25 kg crystallized sorbitol is continuously fed via a powder metering device marketed by K-tron, at a flow rate of approximately 15 kg/h, with a crystallized sorbitol marketed by the Applicant under the trade name NEOSORB®, in order to obtain an average diameter of particles of 180 µm.

In addition, the continuous fluidized air bed granulator is fed with the sorbitol solution via a two-fluid spray nozzle at a flow rate of 15 kg/h.

Spraying of the melt is carried out by air at 110° C. under a pressure of 4.5 bars.

The air used for placing the granulated sorbitol in suspension has a flow rate of approximately 800 m³/h and a temperature adjusted so that the temperature in the fluidized air bed is 80° C.

The granulated sorbitol is continuously discharged via the classifying discharge pipe (the air flow rate in the pipe is adjusted to 60 m³/h in order to obtain the correct final particle size) in a fluidized air bed in order to be cooled from 80° C. to 20° C. over one hour.

The granulated and cooled product is then continuously sieved on a rotary sieve equipped with two metal sieves of 100 and 500 µm.

The fines, the crushed rejects and a fraction of the product obtained between 100 and 500 µm, itself also crushed, (crushing carried out in order to obtain an average recycling particle size of the order of 180 µm) are recycled to the start of granulation in order to maintain a total recycling flow of 15 kg/h.

The granulated sorbitol thus obtained has the characteristics shown in Table IV below.

TABLE IV

| Parameters | Granulated sorbitol of the invention |
|---|---|
| DSC analyses: | |
| γ form | |
| ΔHf (J/g) | 167 |
| Tf | 98.9 |
| Other forms | |
| ΔHf (J/g) | <1 |
| Specific surface area according to BET (m²/g) | 2.3 |
| Compressibility (N) (ERWEKA hardness of the tablets) | 280 |
| Average diameter LASER (μm) | 303 |
| Hygroscopicity | 1.63 |
| Density (g/l) | 505 |
| Free flow (s) | 10 |

Example 5

An AGT 400-type fluidized air bed granulator previously loaded with 25 kg crystallized sorbitol is continuously fed via a powder metering device marketed by K-tron, at a flow rate of approximately 13 kg/h, with a crystallized sorbitol marketed by the Applicant under the trade name NEOSORB®, in order to obtain an average diameter of particles of 450 μm.

In addition, the continuous fluidized air bed granulator is fed, via a two-fluid spray nozzle at a flow rate of 17 kg/h, with a sorbitol solution having 70% of dry matter at a temperature of 60° C.

Spraying of the solution is carried out by air at 90° C. under a pressure of 2.5 bars.

The air used for placing the granulated sorbitol in suspension has a flow rate of approximately 900 m³/h and a temperature adjusted so that the temperature in the fluidized air bed is 67° C.

The granulated sorbitol is continuously discharged via the classifying discharge pipe (the air flow rate in the tube is adjusted to 130 m³/h in order to obtain the correct final particle size) in a fluidized air bed in order to provide cooling from 67° C. to 20° C. over one hour.

The granulated and cooled product is then continuously sieved on a rotary sieve equipped with two metal sieves of 400 and 1300 μm.

The fines, the crushed rejects and a fraction of the product obtained between 400 and 1300 μm, itself also crushed, (crushing carried out in order to obtain an average recycling particle size of the order of 450 μm) are recycled to the start of granulation in order to maintain a total recycling flow of 13 kg/h.

The granulated sorbitol thus obtained has the characteristics shown in Table V below.

TABLE V

| Parameters | Granulated sorbitol of the invention |
|---|---|
| DSC analyses: | |
| γ form | |
| ΔHf (J/g) | 173 |
| Tf | 99.0 |
| Other forms | |
| ΔHf (J/g) | — |
| Specific surface area according to BET (m²/g) | 3.3 |
| Compressibility (N) (ERWEKA hardness of the tablets) | 300 |
| Average diameter LASER (μm) | 880 |
| Hygroscopicity | 1.20 |
| Density (g/l) | |
| Free flow (s) | |

Example 6

In Table VI below, the granulated sorbitols of Examples 1 to 4 are compared with granulated sorbitols known elsewhere.

TABLE VI

| | Granulated sorbitol Example 1 | Granulated sorbitol Example 2 | Granulated sorbitol Example 3 | Granulated sorbitol Example 4 | Granulated sorbitol Example 5 | KARION P 300 Merck | Sorbitol prepared according to EP 1,008,602 |
|---|---|---|---|---|---|---|---|
| Specific surface area according to BET (m²/g) | 2.4 | 2.9 | 2.6 | 2.3 | 3.3 | 3.4 | 2.4 |
| Compressibility (N) (ERWEKA hardness of the tablets) | 270 | 275 | 340 | 280 | 300 | 320 | 275 |
| Average diameter LASER (μm) | 338 | 270 | 328 | 303 | 880 | 220 | 155 |
| Hygroscopicity | 1.10 | 1.11 | 1.85 | 1.63 | 1.20 | 2.40 | 1.3 |
| Density (g/l) | 483 | 523 | 470 | 505 | 410 | 473 | 500 |
| Free flow (s) | 12 | 7 | 11 | 10 | 18 | 7 | 6 |

The granulated sorbitols according to the invention, in contrast to the products of the prior art, all have excellent functional properties which make them suitable for use without drawbacks as excipients and non-hydroscopic additive media, in particular in the food and pharmaceutical fields and industrial applications (for example in detergent tablet applications)

Example 7

The hardness of tablets manufactured with the granulated sorbitol according to the invention of Example 1, containing a commercially-available flavouring and a sweetener, is assessed.

The composition of the tablets expressed in % by weight of the tablet, is given in Table VII below:

TABLE VII

| | |
|---|---|
| Granulated sorbitol of the invention | 98.1% |
| GIVAUDAN liquid mint flavouring | 1% |
| ASPARTAM ® | 0.2% |
| Magnesium stearate | 0.7% |

The tablets are round, having bi-convex faces with a diameter of 8 mm and a thickness of 4.5 mm. The hardnesses of the thus-manufactured tablets are measured for two separate tablet weights, while keeping the thickness constant. The results obtained are shown in Table VIII below:

TABLE VIII

| | Tablet 1 | Tablet 2 |
|---|---|---|
| Weight (mg) | 231 | 253 |
| ERWEKA TBH30GMD hardness (N) | 183 | 327 |

It is apparent that an increase in the weight of the tablet of just 9.5% makes it possible to increase its hardness considerably (79%), leading to a remarkable gain in hardness without the necessity to introduce a large additional quantity of material.

This result constitutes a not inconsiderable saving for the potential user.

The invention claimed is:

1. A granulated sorbitol in essentially γ crystalline form comprising:
   a high sorbitol content,
   a specific surface area, determined according to the BET process, greater than or equal to 2 $m^2/g$,
   a compressibility comprised between 200 and 400 N,
   a volume average diameter measured by LASER diffraction granulometry using a dry-route module comprised between 260 and 1000 µm.

2. The sorbitol according to claim 1 further comprising a hygroscopicity value determined by a change in weight of the sorbitol between 60% and 0% relative humidity.

3. The sorbitol according to claim 1 further comprising a density comprised between 350 and 650 g/l.

4. The sorbitol according to claim 1, wherein the sorbitol has a free-flow, determined according to the process of the European Pharmacopoeia 5.0, volume 1, 01/2005: 20916article 2.9.16, comprised between 5 and 20 seconds.

5. A process for preparing the granulated sorbitol according to claim 1 comprising a step of spraying a sorbitol melt onto a crystallized sorbitol in a fluidized air bed granulator.

6. The process according to claim 5 comprising the steps of:
   a) optionally, concentrating by evaporation, a solution having a sorbitol dry matter content greater than 65%, in order to obtain a solution having a high dry matter content or a melt,
   b) introducing into a fluidized air bed granulator having a discharge pipe, said sorbitol melt or said sorbitol solution with a high dry matter content with a crystallized sorbitol in a ratio by weight of crystallized sorbitol: sorbitol melt or sorbitol solution with a high dry matter content greater than 0.5 :1,
   c) granulating the crystallized sorbitol with said melt, at a fluidized air bed temperature greater than 65° C.,
   d) recovering the granulated product thus obtained via the discharge pipe,
   e) cooling said granulated product thus obtained at ambient temperature, for a duration comprised between 30 minutes and 2 hours,
   f) sieving and recovering the granulated sorbitol thus obtained.

7. The process according to claim 6 comprising the following subsequent step:
   g) recycling the fines, crushed rejects and a fraction of the granulated sorbitol thus obtained in order to maintain a ratio by weight of sorbitol powder:sorbitol melt or sorbitol solution with a high dry matter content greater than 0.5:1.

8. A composition in tablet form comprising as sweetener, texturizer, excipient or as an additive medium the granulated sorbitol according to claim 1.

9. A tablet manufactured from the granulated sorbitol according to claim 1.

* * * * *